(12) United States Patent
Qiu et al.

(10) Patent No.: US 9,447,067 B2
(45) Date of Patent: Sep. 20, 2016

(54) METHOD OF PREPARING INTERMEDIATE OF SALMETEROL

(71) Applicant: AMPHASTAR PHARMACEUTICALS INC., Rancho Cucamonga, CA (US)

(72) Inventors: Yinhua Qiu, Nanjing (CN); Zhengyuan Wu, Nanjing (CN); Song Chen, Nanjing (CN); Haoning Zhang, Nanjing (CN)

(73) Assignee: Amphastar Pahmaceuticals, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/714,196

(22) Filed: May 15, 2015

(65) Prior Publication Data

US 2016/0096816 A1    Apr. 7, 2016

Related U.S. Application Data

(60) Provisional application No. 62/059,791, filed on Oct. 3, 2014.

(51) Int. Cl.
*C07D 319/08* (2006.01)
*C07C 213/00* (2006.01)

(52) U.S. Cl.
CPC ........... *C07D 319/08* (2013.01); *C07C 213/00* (2013.01)

(58) Field of Classification Search
CPC .................................................. C07D 319/08
See application file for complete search history.

(56) References Cited

U.S. PATENT DOCUMENTS

| | | | |
|---|---|---|---|
| 4,992,474 A | 2/1991 | Skidmore et al. | |
| 6,388,134 B1 | 5/2002 | Bessa Bellmunt et al. | |
| 8,648,214 B2 | 2/2014 | Gore et al. | |
| 2010/0009950 A1 | 1/2010 | Gant et al. | |

FOREIGN PATENT DOCUMENTS

| | | | | |
|---|---|---|---|---|
| CN | 103435505 A | | 12/2013 | |
| CN | 103923058 A | * | 7/2014 | ........... C07D 319/08 |
| GB | 2176476 A | | 12/1986 | |

OTHER PUBLICATIONS

Jnaneshwara, G. K. J. Chem. Research (s) (1998) 160-161.*
Reichardt, Christian. Solvents and Solvent Effects in Organic Chemistry. 3rd ed. Wiley-VCH. (2003) 418-420.*
Bream, Robert N., et al., "A mild, enantioselective synthesis of (R)-salmeterol via sodium borohydride-calcium chloride asymmetric reduction of a phenacyl phenylglycinol derivative," J. Chem. Soc., Perkin Trans., 1, 2002, pp. 2237-2242.
Procopiou, Panayiotis A., et al., "Enantioselective synthesis of (S)-salmeterol via asymmetric reduction of azidoketone by *Pichia angusta*," Tetrahedron: Asymmetry, 12, 2001, pp. 2005-2008.
Zhou, D., et al., "New synthetic route to salmeterol," Chinese Journal of Medicinal Chemistry, vol. 19, No. 2, Apr. 2009, pp. 123-125.
Zhigan J., et al., "Synthesis Asthma Drug Salmeterol", Journal of East China Normal University (Natural Science), No. 3, Sep. 2003, pp. 102-104 (English Translation, 9 pages).
Guo, Zong-Liang et al., "Enantioselective synthesis of (R)-salmeterol employing an asymmetric Henry reaction as the key step," Tetrahedron: Asymmetry, Jul. 15, 2011, vol. 22, No. 13, pp. 1395-1399.
Procopiou, Panayiotis A., et al., "The discovery of long-acting saligenin $\beta_2$ adrenergic receptor agonists incorporating a urea group," Bioorganic & Medicinal Chemistry, Oct. 15, 2011, vol. 19, No. 20, pp. 6026-6032.
PCT International Search Report and Written Opinion of the International Searching Authority dated Dec. 4, 2015 of the corresponding International Application No. PCT/US2015/053347.

* cited by examiner

*Primary Examiner* — Golam M M Shameem
*Assistant Examiner* — Laura Daniel
(74) *Attorney, Agent, or Firm* — Lewis Roca Rothgerber Christie LLP

(57) ABSTRACT

A method of preparing an intermediate of salmeterol (Compound 1, 2-amino-1-(2,2-dimethyl-4H-1,3-benzodioxin-6-yl)ethanol) includes: reacting compound 2 with 2-methoxypropene in a first organic solvent to produce a reaction solution including compound 3, compound 2 including a 2-bromo precursor of Compound 1; reacting compound 3 with a nitrogen source to produce compound 4; reacting compound 4 with sodium borohydride in a second organic solvent to produce compound 5; and debenzylating compound 5 by ammonium formate/palladium-carbon catalytic transfer hydrogenation in a third organic solvent to produce Compound 1. A method of preparing salmeterol includes preparing Compound 1, and reacting Compound 1 to prepare salmeterol.

21 Claims, No Drawings

METHOD OF PREPARING INTERMEDIATE OF SALMETEROL

CROSS-REFERENCE TO RELATED APPLICATION

This application claims priority to and the benefit of related U.S. Provisional Application Ser. No. 62/059,791, filed in the U.S. Patent and Trademark Office on Oct. 3, 2014, the entire content of which is incorporated herein by reference.

BACKGROUND

1. Field

The following description is related to a process for the preparation of a reaction intermediate of salmeterol, e.g., Compound 1, 2-amino-1-(2,2-dimethyl-4H-1,3-benzodioxin-6-yl)ethanol.

2. Background

Salmeterol is a long-acting $\beta_2$-adrenergic receptor agonist drug that is prescribed for the treatment of asthma and chronic obstructive pulmonary disease (COPD). It is available as a dry powder inhaler that releases a powdered form of the drug.

The structure of salmeterol is illustrated as follows:

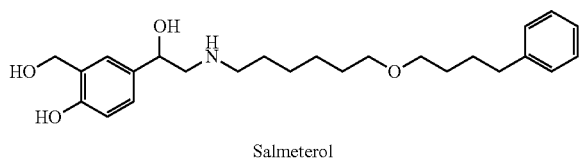 [SMILES: OCc1cc(C(O)CNCCCCCCOCCCCc2ccccc2)ccc1O]

Salmeterol

Salmeterol may be synthesized by reacting an intermediate a with an intermediate b. The intermediate a, intermediate b, and the synthesis route for the forgoing synthesis may be generally illustrated as follows:

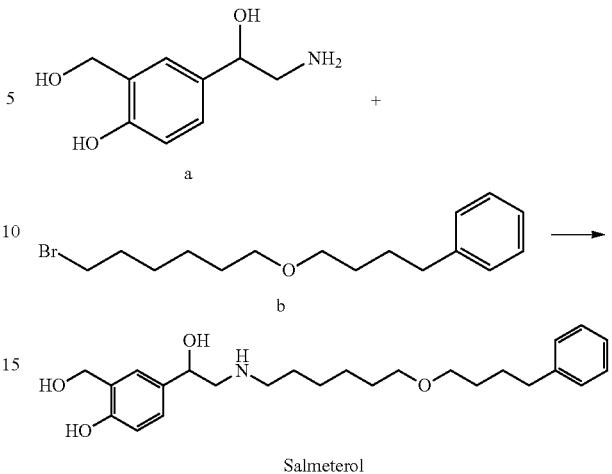

However, this synthesis route leads to the generation of impurities D and G, the structure of each of which is illustrated below. These two impurities are difficult to remove, and therefore, the quality of the salmeterol product is affected by these impurities.

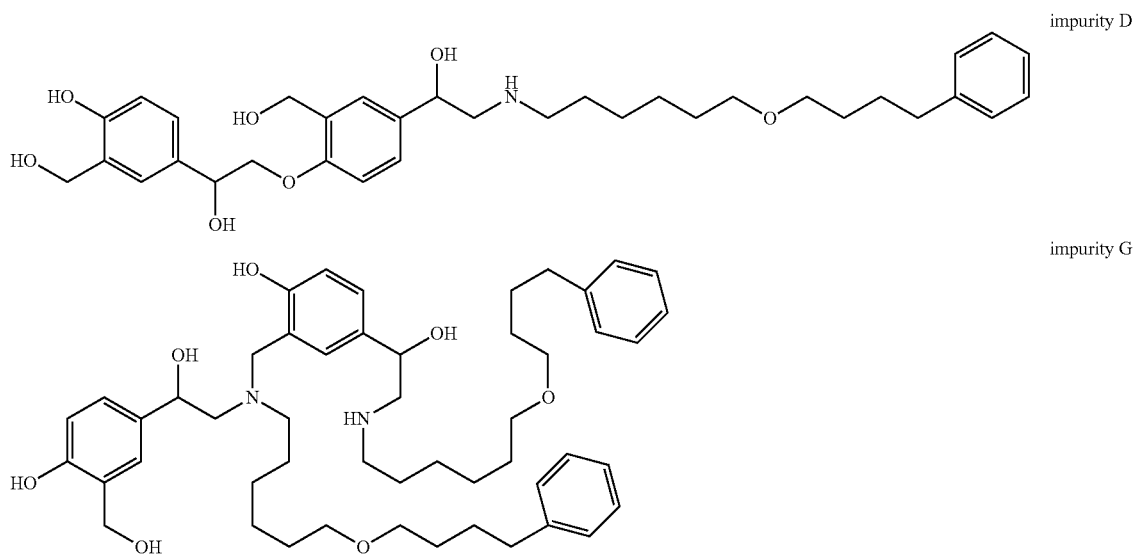

Salmeterol may also be synthesized by reacting intermediate Compound 1, e.g., 2-amino-1-(2,2-dimethyl-4H-1,3-benzodioxin-6-yl)ethanol with the long chain intermediate b or other similar compounds, while intermediate Compound 1 is protected utilizing the hydroxyl group. This process may reduce the production of impurities D and G.

The structure of Compound 1, e.g., 2-amino-1-(2,2-dimethyl-4H-1,3-benzodioxin-6-yl)ethanol, is illustrated below:

compound 1

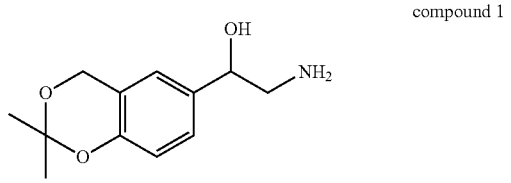 [SMILES: CC1(C)OCc2cc(C(O)CN)ccc2O1]

Compound 1, 2-Amino-1-(2,2-dimethyl-4H1,3-benzodioxin-6-yl)ethanol, may be synthesized utilizing dibenzylamine, sodium azide, and/or phenylglycinol as a nitrogen source (or aminating agent) and utilizing hydrogen as a source of hydrogenation for debenzylation and/or reduction. For example, Compound 1 may be synthesized as follows:

Compound 1 may be prepared utilizing dibenzylamine as the nitrogen source, followed by debenzylation by hydrogenation; utilizing sodium azide as the nitrogen source, followed by reduction by hydrogenation; utilizing nitromethane as the nitrogen source, followed by reduction by sodium borohydride; or utilizing phenylglycinol as the nitrogen source, followed by debenzylation by hydrogenation, etc. Such processes, however, are dangerous and difficult to industrialize.

Compound 1 may also be obtained through a five-step chemical reaction in which p-hydroxybenzaldehyde is utilized as the starting material and nitromethane is utilized as the nitrogen source. However, the stepwise percent yield for the reaction with nitromethane is only 62% (percent yield=actual yield÷theoretical yield×100) due to the weak nucleophilicity of nitromethane, which severely lowers the yield of the whole reaction.

SUMMARY

Aspects of embodiments of the present disclosure generally relate to a process for the preparation of an intermediate (e.g., Compound 1) of salmeterol. By utilizing embodiments of the process of preparing the intermediate, salmeterol may be obtained without impurities D and G. The novel process provides improved yield (e.g., a percent yield of salmeterol of about 45% or more, such as a percent yield of 45% to 100%, where percent yield=actual yield÷theoretical yield× 100) and a highly purified product (e.g., a purity of salmeterol of 98% or more, such as a purity of 98% to 100%, where the % of salmeterol is calculated from the peak area of the salmeterol measured by high performance liquid chromatography), and is facile, efficient, economic and easy to industrialize.

According to an embodiment of the present disclosure, a method of preparing an intermediate of salmeterol (e.g., Compound 1, 2-amino-1-(2,2-dimethyl-4H-1,3-benzodioxin-6-yl)ethanol) includes: reacting compound 2 with 2-methoxypropene in a first organic solvent to produce a reaction solution including compound 3, compound 2 including a 2-bromo precursor of Compound 1; reacting compound 3 with a nitrogen source in the reaction solution to produce compound 4; reacting compound 4 with sodium borohydride in a second organic solvent to produce compound 5; and debenzylating compound 5 by ammonium formate/palladium-carbon catalytic transfer hydrogenation in a third organic solvent to produce Compound 1.

The first organic solvent may include tetrahydrofuran, dichloromethane, acetic ether, methyl tert-butyl ether, chloroform, methyl acetate, or a mixture thereof. The first organic solvent may include tetrahydrofuran.

The reacting of compound 2 with 2-methoxypropene may be conducted in the presence of a catalyst. The catalyst may include p-Toluenesulfonic acid.

The nitrogen source may include α-phenylethylamine.

The reacting of compound 3 with the nitrogen source may be conducted in the presence of a catalyst. The catalyst may include N,N-Diisopropylethylamine.

A weight ratio of α-phenylethylamine to compound 2 may be about 0.5:1 to about 1.5:1. The weight ratio of α-phenylethylamine to compound 2 may be about 0.8:1.

The reacting of compound 3 with the nitrogen source may be conducted at a temperature from about 0° C. to about 50° C. The temperature may be from about 10° C. to about 20° C.

A weight ratio of ammonium formate to compound 5 may be about 0.5:1 to about 5:1. The weight ratio may be about 1.5:1.

A weight ratio of palladium-carbon to compound 5 may be about 0.1:1 to about 0.5:1. The weight ratio may be about 0.2:1.

The third organic solvent may include methanol, ethanol, tetrahydrofuran, isopropanol, or a mixture thereof. The third organic solvent may include a mixture of methanol and tetrahydrofuran.

A volume ratio of methanol to tetrahydrofuran may be about 0.5:1 to about 1.5:1. The volume ratio of methanol to tetrahydrofuran may be about 1:1.

A method of preparing salmeterol includes preparing Compound 1; and reacting Compound 1 to prepare salmeterol.

In some embodiments, compound 2 includes Compound 2, 2-bromo-1-[4-hydroxy-3-(hydroxymethyl)phenyl]ethan-1-one.

In some embodiments, compound 3 includes Compound 3, 2-bromo-1-(2,2-dimethyl-4H-1,3-benzodioxin-6-yl)ethanone.

In some embodiments, compound 4 includes Compound 4, 1-(2,2-dimethyl-4H-1,3-benzodioxin-6-yl)-2-[methyl-1-phenylethylamino]ethanone.

In some embodiments, compound 5 comprises Compound 5, 1-(2,2-dimethyl-4H-1,3-benzodioxin-6-yl)-2-[methyl-1-phenylethylamino]ethanol.

The method according to one or more embodiments of the present disclosure has the following enhanced features:

Compared with other existing technologies, the method according to one or more embodiments of the present disclosure utilizes α-phenylethylamine as the nitrogen source to prepare Compound 1, which is less expensive than dibenzylamine, the raw material generally utilized by other technologies.

Compared with the existing methods of hydrogenation for debenzylation, the method according to one or more embodiments of the present disclosure utilizes ammonium formate/palladium-carbon for catalytic transfer hydrogenation for debenzylation, which is safer, more controllable, environmentally friendly and easier to industrialize.

DETAILED DESCRIPTION

The following detailed description is provided only for purposes of illustration of embodiments of the present disclosure and not for purposes of limiting the scope of the present invention. Alternate embodiments will be readily apparent to those of skill in the art and are intended to be included within the scope of the present invention.

Compound 1 is utilized as an intermediate product (e.g., a reaction intermediate) in embodiments of a process of preparing salmeterol. Compound 1, 2-amino-1-(2,2-dimethyl-4H-1,3-benzodioxin-6-yl)ethanol, may include may include 2-amino-1-(2,2-dimethyl-4H-1,3-benzodioxin-6-yl) ethanol in its substituted or unsubstituted form. For example, the 2-amino-1-(2,2-dimethyl-4H-1,3-benzodioxin-6-yl) ethanol of Compound 1 may be substituted with any suitable functional group (e.g., a protecting group, such as a hydroxyl group, or another labile group) generally available in the art. The substituents of the substituted form of 2-amino-1-(2,2-dimethyl-4H-1,3-benzodioxin-6-yl)ethanol should be apparent to those of ordinary skill in the art, and therefore, will not be described further here. Compound 1, in its unsubstituted form, is illustrated as follows:

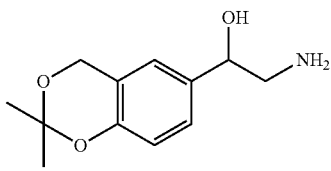

compound 1

According to an embodiment of the present disclosure, a method of preparing an intermediate of salmeterol (e.g., Compound 1, 2-amino-1-(2,2-dimethyl-4H-1,3-benzodioxin-6-yl)ethanol) includes: reacting compound 2 (e.g., a 2-bromo precursor of Compound 1, such as Compound 2, 2-bromo-1-[4-hydroxy-3-(hydroxymethyl)phenyl]ethan-1-one) with 2-methoxypropene in a first organic solvent in the presence of catalyst p-toluenesulfonic acid to produce a reaction solution including compound 3 (e.g., Compound 3, 2-bromo-1-(2,2-dimethyl-4H-1,3-benzodioxin-6-yl)ethanone); reacting compound 3 with a nitrogen source (e.g., α-phenylethylamine) in the above reaction solution (e.g., in the presence of catalyst N,N-Diisopropylethylamine) to produce compound 4 (e.g., Compound 4, 1-(2,2-dimethyl-4H-1,3-benzodioxin-6-yl)-2-[methyl-1-phenylethylamino]ethanone); reacting compound 4 with sodium borohydride in an organic solvent to produce compound 5 (e.g., Compound 5, 1-(2,2-dimethyl-4H-1,3-benzodioxin-6-yl)-2-[methyl-1-phenylethylamino]ethanol); and debenzylating compound 5 by ammonium formate/palladium-carbon catalytic transfer hydrogenation in a third organic solvent to produce Compound 1. The catalyst palladium-carbon may be a 10 weight % palladium loading on activated carbon support, e.g., 10 weight % Pd/C, based on the total weight of the palladium and the activated carbon support. A synthesis route according to the current embodiment is shown in Reaction Scheme 1:

Reaction Scheme 1: a synthesis route of an embodiment of preparing intermediate Compound 1 of salmeterol

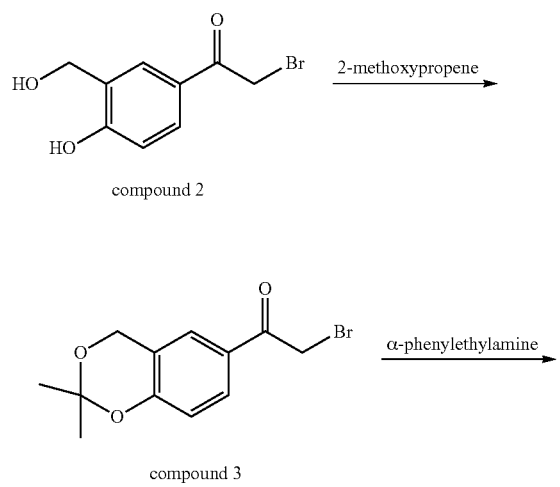

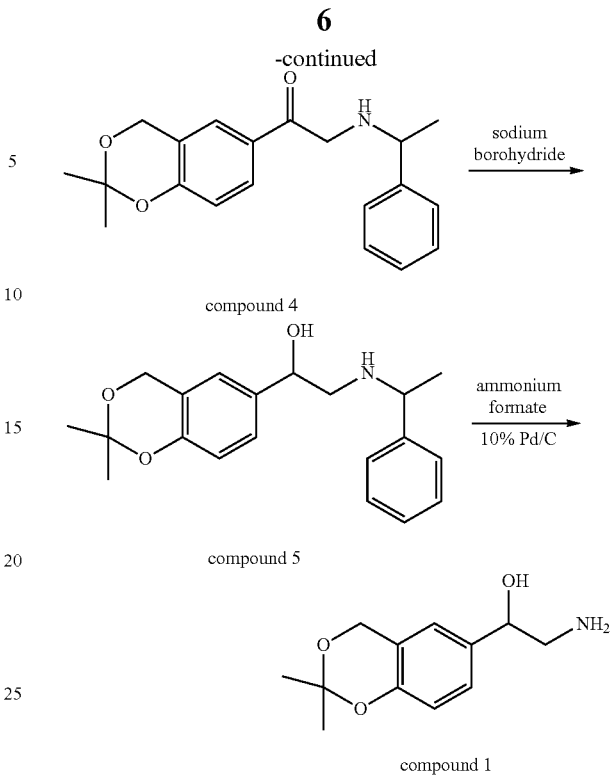

In Reaction Scheme 1, compound 2 (a 2-bromo precursor of Compound 1) is reacted with 2-methoxypropene in an organic solvent to obtain compound 3. The organic solvent may include tetrahydrofuran, dichloromethane, acetic ether, methyl tert-butyl ether, chloroform, methyl acetate, or a mixture thereof. For example, the organic solvent may include tetrahydrofuran. Here, a catalyst may also be utilized for faster reaction rate. For example, p-Toluenesulfonic acid may be utilized as the catalyst.

Compound 3 is then reacted with α-phenylethylamine to produce compound 4. A weight ratio of α-phenylethylamine to compound 2 may be about 0.5:1 to about 1.5:1 (e.g., about 0.8:1). Here, a catalyst may also be utilized for faster reaction rate. For example, N,N-Diisopropylethylamine may be utilized as the catalyst. The reaction may be conducted at a temperature of 0 to 20° C.

Compound 4 is reduced by sodium borohydride to obtain compound 5. This reaction may be carried out in an organic solvent. For example, methanol may be utilized as the organic solvent.

Finally, compound 5 is converted to Compound 1 through catalytic transfer hydrogenation to debenzylation in an organic solvent. The organic solvent may include tetrahydrofuran, methanol, ethanol, isopropanol, or a mixture thereof. For example, the organic solvent may include a blend (mixture) of methanol and tetrahydrofuran.

EXAMPLES

The following examples provide further details of certain embodiments of the current disclosure. The examples are provided to illustrate embodiments of the present disclosure, but the present invention is not limited thereto. Certain features of Reaction Scheme 1 are embodied in the following examples:

Example 1

Preparation of Compound 3

0.5 kg of compound 2 (solution 1) and 2.5 g p-Toluenesulfonic acid (solution 2) were added into 4 L of THF (tetrahydrofuran) at a temperature of −10 to 10° C. to form a reaction solution. 0.36 kg of 2-methoxypropene solution was then added dropwise into the reaction solution. The reaction solution was set for 1 hour to complete the reaction to obtain the compound 3 solution.

Example 2

Preparation of Compound 4

0.43 kg of N,N-Diisopropylethylamine was added into the compound 3 solution to form a reaction solution. The reaction solution was stirred for uniformity at 0-20° C. under $N_2$ protection (an $N_2$ atmosphere). 0.4 kg of α-phenylethylamine was added to the reaction solution. The reaction solution was stirred for another 3 hours and then, after the 3 hours of stirring, filtered to separate away the solids. The mother liquor was collected by evaporating the THF solvent at 35-40° C. and 0.5 kg of yellow oily compound 4 was finally obtained.

Example 3

Preparation of Compound 5

0.5 kg of compound 4 was added into 2 L of methanol and stirred until it was dissolved at a temperature of 5-10° C. to form a reaction solution. 0.2 kg of sodium borohydride was slowly added to the reaction solution under $N_2$ protection (an $N_2$ atmosphere). The reaction solution was then substantially continuously stirred for another 2 hours, followed by extractive filtration. The filter cake was washed with 0.3 L of methanol; washed again with 1.2 L of water; and vacuum dried at 50° C. 0.3 kg of a whitish solid of compound 5 was finally obtained.

Example 4

Preparation of Compound 1

0.3 kg of compound 5, 0.45 kg of ammonium formate and 0.18 kg of 10 weight % Pd/C (based on the total weight of the palladium and the activated carbon support) having a 67 weight % water content (based on the total weight of the palladium, the activated carbon support, and water) were added into an organic solvent blend (mixture) of 2 L of methanol and 2 L of THF to form a reaction solution. The reaction solution was then refluxed for another 10 hours, and subsequently cooled down to 50° C. Pd/C was then removed through filtration. The reaction solution was then subjected to extractive filtration. The filter cake was washed with 0.3 L of methanol and vacuum dried at 50° C. 0.2 kg of a whitish solid of Compound 1 was finally obtained.

Compound 1 may then be utilized to obtain salmeterol according to any suitable method in the art. For example, Compound 1 may be reacted with the long chain intermediate b or other similar compounds to obtain salmeterol.

Compared with other methods of preparing the same types of reaction intermediates, Compound 1 has the desired features of significantly reducing the impurities D and G to improve the quality of the final product. The process for obtaining Compound 1 according to one or more embodiments of the present disclosure improves the safety of production and increases the yield. For example, impurity D may be reduced to 0.03% or less, impurity G may be reduced to 0.02% or less, and the purity of salmeterol may be increased to 99.96%, where the % of the impurities is calculated from the respective peak areas of the impurities, and the % of the salmeterol is calculated from the peak area of the salmeterol, as measured by high performance liquid chromatography. Throughout the present disclosure, references to "%" of a compound indicate a peak area (area %) of the compound relative to the total peak area as measured by high performance liquid chromatography (HPLC) for a sample including the compound, unless the context clearly indicates otherwise. For example, a sample including at least 98% or more of salmeterol may provide a peak area of at least 98% relative to the total peak area of the sample including the salmeterol, as measured by HPLC. In some embodiments, the percent yield of salmeterol from Compound 1 is about 20% (percent yield=actual yield÷theoretical yield×100). Further, by utilizing α-phenylethylamine as the nitrogen source, ammonium formate/palladium-carbon is utilized for catalytic transfer hydrogenation for debenzylation. The method according to one or more embodiments of the present disclosure is simple, environmentally friendly and easy to industrialize.

While the present invention has been described in connection with certain embodiments, it is to be understood that the invention is not limited to the disclosed embodiments, but, on the contrary, is intended to cover various modifications and equivalent arrangements included within the spirit and scope of the appended claims, and equivalents thereof. Throughout the text and claims, the terms "about" and "substantially" are used as terms of approximation, not terms of degree, and reflect the inherent variation associated with measurement, significant figures, and interchangeability, all as understood by a person having ordinary skill in the relevant art. Also, it is to be understood that throughout this disclosure and the accompanying claims, even values that are not preceded by the term "about" are also implicitly modified by that term, unless otherwise specified.

What is claimed is:

1. A method of preparing Compound 1, 2-amino-1-(2,2-dimethyl-4H-1,3-benzodioxin-6-yl)ethanol, the method comprising:
    reacting Compound 2, 2-bromo-1-[4-hydroxy-3-(hydroxymethyl) phenyl]ethan-1-one, with 2-methoxypropene in a first organic solvent to produce a reaction solution comprising Compound 3, 2-bromo-1-(2,2-dimethyl-4H-1,3-benzodioxin-6-yl)ethanone;
    reacting Compound 3 with a nitrogen source in the reaction solution to produce Compound 4, 1-(2,2-dimethyl-4H-1,3-benzodioxin-6-yl)-2-[methyl-1-phenylethylamino] ethanone;
    reacting Compound 4 with sodium borohydride in a second organic solvent to produce Compound 5, 1-(2,2-dimethyl-4H-1,3-benzodioxin-6-yl)-2-[methyl-1-phenylethylamino]ethanol; and
    debenzylating Compound 5 by ammonium formate/palladium-carbon catalytic transfer hydrogenation in a third organic solvent to produce Compound 1.

2. The method of claim 1, wherein the first organic solvent comprises tetrahydrofuran, dichloromethane, acetic ether, methyl tert-butyl ether, chloroform, methyl acetate, or a mixture thereof.

3. The method of claim 1, wherein the first organic solvent comprises tetrahydrofuran.

4. The method of claim 1, wherein the reacting of Compound 2 with 2-methoxypropene is conducted in the presence of a catalyst.

5. The method of claim 4, wherein the catalyst comprises p-Toluenesulfonic acid.

6. The method of claim 1, wherein the nitrogen source comprises α-phenylethylamine.

7. The method of claim 6, wherein the reacting of Compound 3 with the nitrogen source is conducted in the presence of a catalyst.

8. A method of preparing Compound 1, 2-amino-1-(2,2-dimethyl-4H-1,3-benzodioxin-6-yl)ethanol, the method comprising:
  reacting Compound 2, 2-bromo-1-[4-hydroxy-3-(hydroxymethyl) phenyl]ethan-1-one, with 2-methoxypropene in a first organic solvent to produce a reaction solution comprising Compound 3, 2-bromo-1-(2,2-dimethyl-4H-1,3-benzodioxin-6-yl)ethanone;
  reacting Compound 3 with a nitrogen source in the reaction solution to produce Compound 4, 1-(2,2-dimethyl-4H-1,3-benzodioxin-6-yl)-21[methyl-1-phenyl-ethylamino]ethanone;
  reacting Compound 4 with sodium borohydride in a second organic solvent to produce Compound 5, 1-(2,2-dimethyl-4H-1,3-benzodioxin-6-yl)-2-[methyl-1-phenylethylamino]ethanol; and
  debenzylating Compound 5 by ammonium formate/palladium-carbon catalytic transfer hydrogenation in a third organic solvent to produce Compound 1;
  wherein the reacting of Compound 3 with the nitrogen source is conducted in the presence of a catalyst, and wherein the catalyst comprises N,N-Diisopropylethylamine.

9. The method of claim 6, wherein a weight ratio of α-phenylethylamine to Compound 2 is 0.5:1 to 1.5:1.

10. The method of claim 9, wherein the weight ratio of α-phenylethylamine to Compound 2 is 0.8:1.

11. The method of claim 6, wherein the reacting of Compound 3 with the nitrogen source is conducted at a temperature from 0° C. to 50° C.

12. The method of claim 11, wherein the temperature is from 10° C. to 20° C.

13. The method of claim 1, wherein a weight ratio of ammonium formate to Compound 5 is 0.5:1 to 5:1.

14. The method of claim 13, wherein the weight ratio is 1.5:1.

15. The method of claim 1, wherein a weight ratio of palladium-carbon to Compound 5 is 0.1:1 to 0.5:1.

16. The method of claim 15, wherein the weight ratio is 0.2:1.

17. The method of claim 1, wherein the third organic solvent comprises methanol, ethanol, tetrahydrofuran, isopropanol, or a mixture thereof.

18. The method of claim 17, wherein the third organic solvent comprises a mixture of methanol and tetrahydrofuran.

19. The method of claim 18, wherein a volume ratio of methanol to tetrahydrofuran is 0.5:1 to 1.5:1.

20. The method of claim 19, wherein the volume ratio of methanol to tetrahydrofuran is 1:1.

21. A method of preparing salmeterol, the method comprising:
  reacting Compound 2, 2-bromo-1-[4-hydroxy-3-(hydroxymethyl) phenyl]ethan-1-one, with 2-methoxypropene in a first organic solvent to produce a reaction solution comprising Compound 3, 2-bromo-1-(2,2-dimethyl-4H-1,3-benzodioxin-6-yl)ethanone;
  reacting Compound 3 with a nitrogen source in the reaction solution to produce Compound 4, 1-(2,2-dimethyl-4H-1,3-benzodioxin-6-yl)-2-[methyl-1-phenylethylamino]ethanone;
  reacting Compound 4 with sodium borohydride in a second organic solvent to produce Compound 5, 1-(2,2-dimethyl-4H-1,3-benzodioxin-6-yl)-2-[methyl-1phenylethylamino]ethanol;
  debenzylating Compound 5 by ammonium formate/palladium-carbon catalytic transfer hydrogenation in a third organic solvent to produce Compound 1,2-amino-1-(2,2-dimethyl-4H-1,3-benzodioxin-6-yl) ethanol; and
  reacting Compound 1 to prepare salmeterol.

* * * * *

UNITED STATES PATENT AND TRADEMARK OFFICE
CERTIFICATE OF CORRECTION

PATENT NO. : 9,447,067 B2  
APPLICATION NO. : 14/714196  
DATED : September 20, 2016  
INVENTOR(S) : Yinhua Qiu et al.

Page 1 of 1

It is certified that error appears in the above-identified patent and that said Letters Patent is hereby corrected as shown below:

On the Title Page

(73) Assignee   Delete "Pahmaceuticals",  
                Insert --Pharmaceuticals--

Signed and Sealed this  
Third Day of April, 2018

Andrei Iancu  
*Director of the United States Patent and Trademark Office*